United States Patent
Arnold et al.

(10) Patent No.: US 9,340,842 B2
(45) Date of Patent: May 17, 2016

(54) REACTOR SYSTEM FOR ELECTROPORATION

(75) Inventors: Jochen Arnold, Worms (DE); Martin Sack, Rheinstetten (DE); Gerhardt Schmidt, Worms (DE); Dirk Epperlein, Stadecken-Elsheim (DE)

(73) Assignee: SUEDZUCKER AKTIENGESELLSCHAFT MANNHEIM/OCHSENFURT (DE)

( * ) Notice: Subject to any disclaimer, the term of this patent is extended or adjusted under 35 U.S.C. 154(b) by 143 days.

(21) Appl. No.: 13/517,948

(22) PCT Filed: Dec. 22, 2010

(86) PCT No.: PCT/EP2010/007854
§ 371 (c)(1),
(2), (4) Date: Jun. 20, 2012

(87) PCT Pub. No.: WO2011/076393
PCT Pub. Date: Jun. 30, 2011

(65) Prior Publication Data
US 2012/0264187 A1    Oct. 18, 2012

(30) Foreign Application Priority Data
Dec. 23, 2009  (EP) .................................... 09015926

(51) Int. Cl.
*C12M 1/42*  (2006.01)
*C13B 10/08*  (2011.01)
(Continued)

(52) U.S. Cl.
CPC .............. *C13B 10/083* (2013.01); *A23N 1/006* (2013.01); *A61N 1/327* (2013.01)

(58) Field of Classification Search
CPC ....... A61N 1/327; A23N 1/006; C12B 10/083
USPC ............................................ 435/173.6, 285.2
See application file for complete search history.

(56) References Cited

U.S. PATENT DOCUMENTS

| 6,178,880 B1 | 1/2001 | Mastwijk et al. ............... 99/451 |
| 2004/0166019 A1 | 8/2004 | Schultheiss ..................... 422/22 |

(Continued)

FOREIGN PATENT DOCUMENTS

| DE | 102004025046 | 12/2005 |
| WO | WO 98/14074 | 4/1998 |
| WO | WO 2006/121397 | 11/2006 |

OTHER PUBLICATIONS

Machine Translation of DE 10 2004 025 046 A1. Translated on Mar. 20, 2013.*

(Continued)

*Primary Examiner* — Michael Hobbs
(74) *Attorney, Agent, or Firm* — Hayes Soloway P.C.

(57) ABSTRACT

A reactor system, for electroporation includes a reactor chamber having a length and a width, whereby the reactor chamber contains a central section along its length. A first pulse generator to which two electrodes (A1) and (A2) are connected are located in the reactor chamber in the central section of the reactor chamber such that they are, when measured in the length direction of the reactor chamber, at least a distance equalling half the width of the reactor chamber apart. A second pulse generator to which two electrodes (B1) and (B2) are connected are located in the reactor chamber in the central section of the reactor chamber such that they are, when measured in the length direction of the reactor chamber, at least a distance equalling half the width of the reactor chamber apart.

18 Claims, 2 Drawing Sheets

(51) Int. Cl.
*A23N 1/00* (2006.01)
*A61N 1/32* (2006.01)

(56) References Cited

U.S. PATENT DOCUMENTS

2008/0060637 A1    3/2008    Arnold et al. .................. 127/4

2008/0279995 A1    11/2008    Schultheiss et al. .......... 426/238

OTHER PUBLICATIONS

International Search Report issued in corresponding PCT application PCT/EP2010/007854 dated Mar. 22, 2011 (3 pgs).

\* cited by examiner

REACTOR SYSTEM FOR ELECTROPORATION

FIELD OF THE INVENTION

The invention relates to a reactor system suitable for electroporation of cells, such as plant cells.

BACKGROUND OF THE INVENTION

Such a reactor system is known from DE-A-10 2004 025 046; in this publication a reactor is disclosed wherein the electrodes of one or more high-voltage pulse generators are located in a reactor chamber, generating an electrical field across the width of the said reactor chamber.

The known reactor system is suitable for the treatment of a large throughput by the use of more than one Marx generator but has the disadvantage that a considerable pulse current may flow out of the reactor chamber in the direction of the flow of the material, e.g. in the case of a voltage application asymmetric to ground. Hence, additional ground electrodes are required for safety reasons. Moreover, the efficiency of the systems is reduced due to regions with considerably low electric field below the threshold necessary for electroporation of cell material.

WO-A-98 4074 discloses a pulsed electric field treatment device for the sterilization and preservation of pumpable food products having at least two electrodes and an insulator. Each electrode includes an electrode flow chamber. The insulator is situated between the electrodes. A high voltage pulse generator applies a high voltage pulse of variable voltage, frequency and pulse duration to the electrodes.

US-A-2008 279995 discloses a process for extracting useful substances from wine grapes by electroporation of the must produced from red and/or white grapes. The must is pumped or circulated before the pressing applied for must production through an installation or part of an installation and pulsed electric fields are applied therein to irreversibly rupture the biological cell walls of the grape skins. The device for carrying out must electroporation comprises a dielectric pipe, the flow duct for the must, in whose wall are arranged two mutually spaced electrodes to form a pulsed electric field between the electrodes. The device shows a strongly inhomogeneous field distribution in the flow volume.

SUMMARY OF THE INVENTION

It is an objective of the present invention to reduce or even eliminate the said disadvantage.

The objective is achieved in that the reactor system comprises:
 a reactor chamber having a length and a width, whereby the reactor chamber contains a central section along its length;
 a first pulse generator to which two electrodes A1 and A2 are connected, whereby the electrodes A1 and A2 are located in the reactor chamber in the central section and such that they are, when measured in the length direction, at least a distance equalling half the width of the reactor chamber apart;
 a second pulse generator to which two electrodes B1 and B2 are connected, whereby the electrodes B1 and B2 are located in the reactor chamber in the central section and such that they are, when measured in the length direction, at least a distance equalling half the width of the reactor chamber apart.

It is an advantage of the reactor system according to the invention that by combining the method of split electrodes with an electric field orientation in the direction of the flow of the material, additional ground electrodes may be omitted.

It is a further advantage of the reactor system according to the invention that the regions—in particular in the central section—where the electric field is not strong enough to be suitable for electroporation can be reduced.

It is another advantage of the reactor system according to the invention that it is also suitable for larger-scale reactors, without having to resort to one single extremely powerful pulse generator.

It is yet another advantage of the reactor system according to the invention that it can be made suitable for processing high mass flows by increasing the width of the reactor chamber, thus avoiding largely or even completely the necessity to increase the velocity of the material conveyed through the reactor system. As is known, an increase of velocity can easily lead to problems such as abrasion of the reactor system, pressure losses, or undesired stresses to the material conveyed through the reactor system.

The present invention relates to a reactor system suitable for electroporation of cells, such as plant cells. The term reactor system as used herein encompasses not only a reactor chamber for carrying out an electroporation process but also all equipment, such as a pulse generator, that is essential for carrying out the said electroporation process in the reactor chamber.

As meant herein, the electroporation that is carried out in the reactor has as purpose to irreversibly disrupt cells that are present in the reactor chamber. The power of the electroporation should therefore be greater as compared to known electroporation processes that are merely aimed at temporarily increasing the permeability of cell membranes without irreversible disruption of cells, a process also referred to as electropermeabilization.

As is known, in electroporation a voltage is applied to two electrodes, resulting in an electric field between these electrodes, whereby a product—i.e. the product to be electroporated—is placed between the electrodes. The applied electric field induces an electric potential across the membrane of cells; this leads to the formation of pores in the membranes, or, in case of the electric field is strong enough, to the destruction of the cell membranes. In the processes that may be executed in the reactor system of the invention, this destructive effect is desirable as it can lead to the release of valuable compounds from the cells; one example thereof is the release of sucrose (sugar) from sugar beet cells.

The reactor system according to the invention comprises a reactor chamber; this is the chamber intended for carrying out an electroporation process. As is usual for reactor chambers, the reactor chamber in the reactor system according to the invention has a length and a width as important dimensions, whereby both the length as well as the width are meant herein to reflect the inner dimensions, i.e. without including dimensions of the material the chamber is constructed from.

The terms length and width as meant herein have the meaning normally associated with them by the person skilled in the art. For example, in case the reactor chamber is in the form of—or approximating—a cylinder, then the length is understood to be the inner distance between the ends that cap the cylinder as measured along the central axis of the cylinder, and the width is understood to be the diameter of the inner circular cross-section of the cylinder. In another example, if the reactor chamber is in the form of—or approximating—a rectangular duct then the length is understood to be the inner distance between the ends of the duct and the width is understood to be the smaller of the two inner dimensions defined by the sides of the rectangular cross-section of the duct. The term cross-section has herein its usual meaning of being the intersection, or 'slice', of a body in 3-dimensional space with a plane.

The reactor chamber should preferably be constructed from a material that is essentially an electrical insulator. This has the advantage that the electrodes, which will be described in more detail below, can be located and fixed in the reactor chamber without the need for further insulating measures.

It is an advantage of the reactor system according to the invention that it may be implemented on commercial industrial scale whereby rather large volumes of a product can be electroporated. In particular, the reactor system of the invention enables the construction of reactor chambers having a large width. Said average width may in an embodiment of the invention vary between 0.05 and 2.00 m. Preferably, the average width of the reactor chamber is at least 0.10, 0.15, 0.20, 0.25 or 0.30 m; the average width of the reactor chamber is preferably at most 2.00, 1.50, 1.40, 1.30, 1.20, 1.10, 1.00, 0.90, 0.80, or 0.75 m.

The length of the reactor chamber may vary within a wide range; in one embodiment, the length lies between 0.75 and 5.0 m, more preferably between 0.80, 0.90. 1.00, 1.10, 1.20, 1.30, 1.40, 1.50 or 2.00 m and 4.5, 4.0, 3.5, or 3.0 m. The length of the reactor chamber is preferably at least equal to the width of the reactor chamber; more preferably, the length of the reactor chamber is at least 1.5, 2.0, 2.5, 3.0, 3.5, 4.0, 4.5, 5.0, 5.5, 6.0, 6.5, 7.0, 7.5, 8.0, 8.5, 9.0, 9.5, or even at least 10 times the width of the reactor chamber. With an increasing ratio of length over width, the maintaining of a substantially homogeneous electrical field becomes more easy to implement.

Although it is an advantage of the present invention that not one pulse generator must carry the whole load, it is nevertheless foreseen that in certain main preferred embodiments of the invention on larger scale the pulse generators must each individually be able to supply at least an average power of 10 kW, 20 kW, 50 kW, 100 kW or 200 kW in order to achieve the desired electroporation effects. It is for example estimated that the electroporation of a total volume of 15,000 ton beet/day in a sugar factory may require an installed capacity of about 400 kW to 700 kW or more. In view of the technical and commercial limitations in the size and power of pulse generators, the reactor system of the invention may be favourably implemented in this type of factory, whereby preferably two, four, or even six or eight pulse generators are used.

The reactor chamber in the reactor system according to the invention has a central section along its length. As meant herein, a central section is a part of the reactor chamber that has the cross-section and at least a portion of the length of the reactor chamber as defining dimensions. In one preferred embodiment, the central section covers the whole of—and is thus identical to—the reactor chamber. In another preferred embodiment, however, the central section does not cover the whole of the reactor chamber; in this embodiment, a section at one end or at both ends of the reactor chamber—as seen in the length dimension—is not part of the central section. The volume of the central section is preferably between 30, 40, or 50 and 95, 90, 80, or 70 vol. % in relation to the volume of the reactor chamber as a whole. The average width of the central section should be within the ranges as given above for the average width of the reactor chamber.

The reactor system according to the invention comprises two pulse generators: a first pulse generator and a second pulse generator. A pulse generator as meant herein is a device capable of producing electrical high-voltage pulses to electrodes that are connected to the pulse generator. Such devices are as such known. One example of such a device is a Marx generator. The reactor system may comprise a third pulse generator, or even one or more further pulse generators. It is preferred that an even number of pulse generators is used; in one preferred embodiment, four pulse generators, preferably Marx generators, are used.

If two or more pulse generators are connected to one single pair of electrodes resulting in a parallel configuration of the generators, oscillations between the pulse generators may occur in the case of a short time delay of one generator with respect to the others, so called jitter. These oscillations can be dampened advantageously by separating at least one electrode and connecting each generator output to one part of the separated electrode only. Hence, the resistance between the separate parts of the electrode may serve as a dampening element. This method is in principle known from literature, e.g. DE 10 2004 025 046 A1. Usually the resistance between two parts of one electrode (e.g. A1 and B1) is in the order of several Ohm up to several 10 Ohm. For the design of an electroporation reactor the ratio of the resistances between the two electrode groups A1 and B1 and the electrode pairs A1 and A2 is of importance. Hence, design rules can be based on the geometry only.

To the first pulse generator, two electrodes are connected, herein named A1 and A2. According to the invention, the electrodes A1 and A2 are located at least partly and preferably essentially completely in the central section of the reactor chamber. The placement of the electrodes A1 and A2 should be such that the electrical field lines that are generated by a pulse fed to A1 and A2 by the first pulse generator can run substantially along the length of the central section. Electrodes A1 and A2 should thus be at a distance from each other when measured in the length direction of the central section. This distance should be at least equal to half the width of the reactor chamber; preferably the distance is more than 50, 60, 70, 80, 90, or even more than 95% of the length of the central section. In one preferred embodiment, electrodes A1 and A2 are located at essentially opposite ends of the length of the central section.

The actual shape of the electrodes A1 and A2 may vary considerably. Preferably, however, they are shaped in such a way that the shape does not negatively influence the functioning of the electroporation process, or even contributes positively to it by helping to ensure an as homogeneous as possible electrical field strength in the central section. One or both of the electrodes A1 and A2 may be in split form. In one embodiment, electrode A1 is split into split-electrodes A1-i and A1-ii, whereby these are placed such that A2 lies between A1-i and A1-ii when evaluated along the length direction. In another embodiment electrode A1 (A2) is split into split-electrodes A1-i and A1-ii (A2-i and A2-ii), whereby these are placed such that A1-i and A1-ii (A2-i and A2-ii) lie on the same position when evaluated along the length direction.

To the second pulse generator, two electrodes are connected, herein named B1 and B2. According to the invention, the electrodes B1 and B2 are located at least partly in the central section of the reactor chamber. The placement of the electrodes B1 and B2 should be such that the electrical field lines that are generated by a pulse fed to B1 and B2 by the first pulse generator can run substantially along the length of the central section. Electrodes B1 and B2 should thus be at a distance from each other when measured in the length direction of the central section. This distance should be at least equal to half the width of the reactor chamber; preferably the distance is more than 50, 60, 70, 80, 90, or even more than 95% of the length of the central section. In one preferred embodiment, electrodes B1 and B2 are located at essentially opposite ends of the length of the central section.

The actual shape of the electrodes B1 and B2 may vary considerably. Preferably, however, they are shaped in such a way that the shape does not negatively influence the functioning of the electroporation process, or even contributes positively to it by helping to ensure an as homogeneous as possible electrical field strength in the central section. One or both of the electrodes B1 and B2 may be in split form. In one embodiment, electrode B1 is split into split-electrodes B1-i and B1-ii, whereby these are placed such that B2 lies between B1-i and B1-ii when evaluated along the length direction. In another embodiment electrode B1 (B2) is split into split-electrodes B1-i and B1-ii (B2-i and B2-ii), whereby these are placed such that B1-i and B1-ii (B2-i and B2-ii) lie on the same position when evaluated along the length direction.

In the present invention it is advantageous if the pulse shapes applied to each pair of electrodes are substantially equal. This may be achieved by means that are as such known such as matching the electrode-pairs' impedances, the impedances of the pulse generators and the connecting circuits, or the total impedances of the circuits. In a simple design this can be achieved by designing all electrodes equal and mounting them in the reactor chamber on a circle along the inner perimeter—whereby the term perimeter has its usual meaning of being a path that surrounds an area—with equal distance to each other, using pulse generators with the same inner impedance and using connecting circuits with the same geometric arrangement.

In one main embodiment, electrodes A1 and B1 are placed such that they are electrically insulated from each other in the case of an empty reactor chamber; similarly, electrodes A2 and B2 are also insulated from each other. In another main embodiment, however, either electrodes A1 and B1 or electrodes A2 and B2 are joined into one combined electrode.

In another embodiment the electrodes A1 and B1 (A2 and B2) are split into split-electrodes and the split-electrodes A1-i, ... A1-i'', B1-i, ... B1-i'' (A2-i, ... A2-i'', B2-i, ... B2-i'') are intermingled, whereby the mentioned electrodes are located in the reactor chamber in the central section and such, that they are, when measured in the length direction, less then a distance equalling half the width of the reactor chamber apart. An example of such a configuration is shown in FIG. 2.

It is preferred that the electrical field lines are distributed as homogeneously as possible in the central section, and that they run essentially in the length direction. It is preferred that electrodes A1 and B1 are located within a short distance from each other when seen along the length of the central section. Preferably, A1 and B1 are located less than 20% or 10% of the width apart from each other along the length of the central section; more preferably, electrode A1 of the first pulse generator is on essentially the same place as electrode B1 of the second pulse generator, when measured along the length direction. Similarly, it is preferred that electrodes A2 and B2 are located within a short distance from each other when seen along the length of the central section. Preferably, A2 and B2 are located less than 20% or 10% of the width apart from each other along the length of the central section; more preferably, electrode A2 of the first pulse generator is on essentially the same place as electrode B2 of the second pulse generator, when measured along the length direction.

Already by having a dimension due to their function, the electrodes will occupy a portion of the inner perimeter of the central section in the reactor chamber. Nevertheless, in case the electrodes are not joined there should be a space of at least 0.5 cm along the inner perimeter between them in order to allow for electrical insulation. Preferably, the said space is at least 1, 2, 3, 4 or even at least 5 cm. It is preferred that the electrodes are shaped in such a way that an electrode occupies/covers at most 50% of the perimeter of the central section, when measured cross-sectionally (i.e. not in the length direction). More preferably, an electrode covers at most 49, 24, 11.5 or even at most 5.25% of the perimeter.

It is preferred that the electrodes cover a portion of the inner perimeter of the central section that is such that electrical field lines can be made to flow even substantially along the length of the central section and/or that the distribution of the electrical field lines can be substantially homogeneous. At the same time, it is preferred, in particular in case it is intended that a product stream flows through the reactor chamber, that the electrodes stand out as little as possible from the perimeter towards the centre of the cross-section; this has the advantage that any flow of a product stream is hindered as little as possible. An electrode should preferably occupy less than 30% of the surface area of the cross section; more preferably, an electrode occupies less than 25, 20, 15, 10, or even less than 5% of the surface area of the cross section.

It is furthermore preferred that the placement of the electrodes A1 and A2, when evaluated along the length direction relative to each other, is not twisted to a great extent. Preferably, the placement of the electrodes A1 and A2 relative to each other along the inner perimeter varies less than 30%, preferably less than 20% or even 10% of the inner perimeter; most preferably, the said placement is essentially identical.

Similarly, it is preferred that the placement of the electrodes B1 and B2, when evaluated along the length direction relative to each other, is not twisted to a great extent. Preferably, the placement of the electrodes B1 and B2 relative to each other along the inner perimeter varies less than 30%, preferably less than 20% or even 10%; most preferably, the said placement is essentially identical.

When the placement along the perimeter of the electrodes A and the electrodes B is substantially or essentially identical, each pair of electrodes then powers a separate segment of the central section as seen along the length of the central section.

In a main embodiment of the invention, both the first and the second pulse generator are high-voltage Marx generators. It is furthermore preferred that the Marx generators have means for triggering; such means are as such known as e.g. referred to in DE-A-10 2004 025 046. The triggering means are preferably such that the Marx generators are ignited synchronously with a temporal uncertainty of not more than 30%, 20%, 10%, or even 5% of the pulse length. This has the advantage that a more stable operation may be achieved. Preferably, the pulse shape of each pair of electrodes is substantially equal.

In another embodiment, the high-voltage Marx generators are bipolar, i.e. symmetric to ground. This involves the advantage of lower voltage to ground and, hence, less effort for insulation to ground. Additional ground electrodes at inlet and outlet and either shorter insulating elements between these electrodes and the high-voltage electrodes are then required or additional losses due to low-filed regions reduce the efficiency. Alternatively, however, it was found that it can be advantageous if the high-voltage Marx generators are unipolar. The main advantage of this solution is, that apart from the mentioned losses no additional ground electrodes at inlet and outlet of the reactor are required. As a consequence, the electroporation reactor can be manufactured with insulating elements of one single type only. This is a cost-effective solution. Moreover, unipolar Marx generators are commonly available on the market.

DE 10 2004 025 046 A1 describes an electroporation chamber of rectangular or square cross section. When connecting such a chamber to a tube system, which typically has a round shaped cross section, connecting elements transferring the round shape to a rectangular or square shape of the same cross section area are required. To omit blocking of the material a smooth transition with constant cross section area is required. The use of a tube-like electroporation reactor with round shaped cross section omits the need for such connecting elements.

The reactor system according to the invention should be suitable for executing an electroporation process on a product, whereby the product preferably contains plant cells. The invention thus also relates to a process for the electroporation of cells, preferably plant cells, whereby the electroporation is done in a reactor system according to the present invention. The electroporation process may according to the invention be executed in batch, or continuously. The shape, form and the location of inlets and outlets attached to the reactor chamber can vary considerably, depending on the way the electroporation process will be executed. For example and as is known, in a batch process an inlet for the product to be electroporated may function at the same time as outlet. In one preferred embodiment, the reactor system is suitable for executing an electroporation process in continuous fashion. In this embodiment, the reactor chamber has an entrance and an exit. The central section lies between the entrance and the exit, such that a stream of a product can be made to flow through the central section on its way from the entrance to the exit. Examples of products that may be subjected to electroporation in this fashion are: sugar beets, an aqueous dispersion of sugar beets, an aqueous dispersion of chips of sugar beet, chicory roots, an aqueous dispersion of chicory roots, and an aqueous dispersion of chips of chicory root.

In one main embodiment of the process for the electroporation of plant cells according to the invention, a product essentially consisting of an aqueous dispersion of chips of sugar beet is made to flow through a reactor chamber in a reactor system according to the invention. Upon entry into the reactor chamber, the conductivity of the aqueous dispersion of chips of sugar beet preferably lies or is adjusted to a value between 0.2 and 10 mS/cm, more preferably between 2 and 6 mS/cm; the pH of the aqueous dispersion of chips of sugar beet preferably lies or is adjusted to a value lying between 7 and 14, more preferably between 9 and 11. The field strength as applied to the product in the central section preferably lies between 0.1 and 20 kV/cm, more preferably between 3 and 6 kV/cm. The electroporation is carried out at a temperature that preferably lies between 0 and 65° C. More preferably the said temperature lies between 10 and 40° C.; this has the advantage that certain beneficial subsequent operations, such as for example the extraction operation as disclosed in WO-A-2006/108481, may be implemented without the need for significant intermediate temperature changes.

BRIEF DESCRIPTION OF THE DRAWINGS

In the Figures.

DETAILED DESCRIPTION OF THE INVENTION

Figure 1:
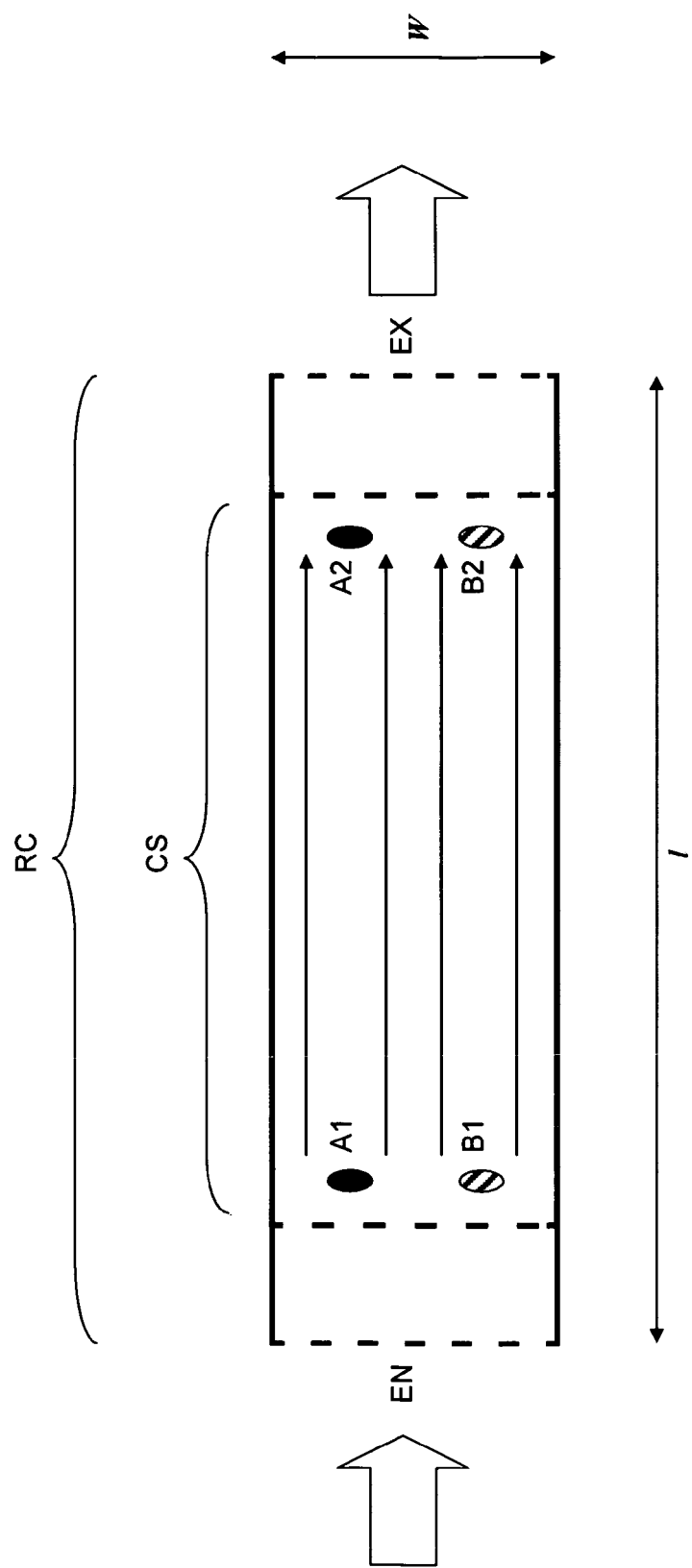
FIG. 1 shows a reactor chamber (RC) according to the invention.

FIG. 1 shows the cross-section of a reactor chamber RC. The RC as shown may have a circular cross-section or be in the shape of a rectangular duct. The RC has a length l and a width W. The RC contains a central section (CS); in the CS, electrodes A1 and A2 are placed in the perimeter, as well as electrodes B1 and B2. A1 and A2 are connected to a first pulse generator (not shown); likewise, B1 and B2 are connected to a second pulse generator (not shown). The RC of FIG. 1 is suitable for continuous operation; a product flow such as for example an aqueous dispersion of chips of sugar beet is made to flow through the entrance EN into the RC, then flow through the CS and then outwards out of the RC via the exit EX. While flowing through the CS, the product is exposed to the pulses of the electrical field that flow between the electrodes A1 and A2, and between B1 and B2. As a result, the product is electroporated. After leaving the RC via the exit EX, the electroporated chips of sugar beet may be subjected to an extraction process in order to recover sugar therefrom.

Figure 2:
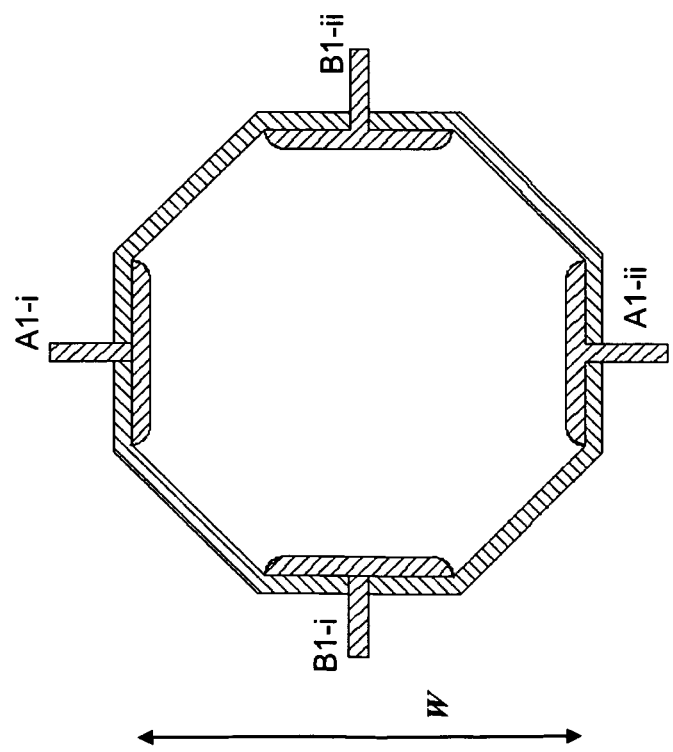
FIG. 2 shows a cross-section of a central section (CS) according to the invention.

FIG. 2 shows a cross-section of a central section (CS) according to an embodiment of the invention, at the location along the length where the electrodes A1 and B1 are placed. In this embodiment, the electrodes A1 and B1 are present in split form; furthermore, the split-electrodes are aligned along the perimeter of the cross section so as to disturb the product flow as little as possible. The width W of the RC, and thus of the CS too, is indicated in FIG. 2 as well.

In this embodiment, the split-electrodes are located near to each other; it is however also possible that the split-electrodes are separated from each other, e.g. in the length direction with then the other electrode (A2 or B2) located in between.

Figure 3:
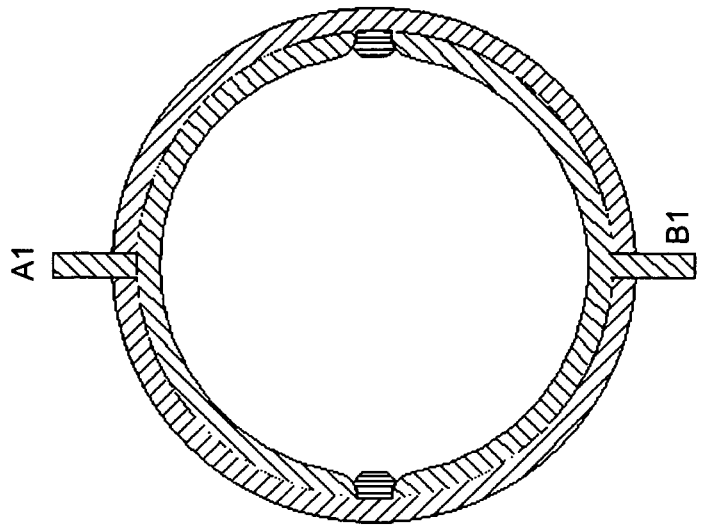
FIG. 3 shows a further cross section of a central section (CS) according to the invention.

FIG. 3 shows a cross-section of a central section (CS) according to a further embodiment of the invention, at the location along the length where the electrodes A1 and B1 are placed. In this embodiment, the electrodes are shaped such that together they cover almost the complete inner perimeter of the CS, with only just enough space between them to allow for electrical insulation.

The invention claimed is:
1. A reactor system, comprising:
a reactor chamber having a length and a width, whereby the reactor chamber contains a central section along its length, wherein the length of the reactor chamber is at least 1.5 times the width of the reactor chamber;
a first pulse generator to which two electrodes (A1) and (A2) are connected, wherein the electrodes (A1) and (A2) are located in the reactor chamber in the central section at essentially opposite ends of the central section such that they are, when measured in the length direction, at least a distance equalling half the width of the reactor chamber apart; and
a second pulse generator to which two electrodes (B1) and (B2) are connected, wherein the electrodes (B1) and (B2) are located in the reactor chamber in the central section at essentially opposite ends of the central section such that they are, when measured in the length direction, at least a distance equalling half the width of the reactor chamber apart,
whereupon electrical field lines from said electrodes run essentially in the length direction of the reactor chamber whereby to produce a homogeneous electrical field the length of the reaction chamber.
2. The reactor system according to claim 1, comprising at least one further pulse generator, whereby two electrodes are connected to any further pulse generator, said electrodes being located in the reactor chamber in the central section and such that the two electrodes of a further pulse generator are, when measured in the length direction, at least a distance equalling half the width of the reactor chamber apart.

3. The reactor system according to claim 1, whereby at least one electrode of the first pulse generator is on the same place as an electrode of the second pulse generator and/or of a further pulse generator, when measured in the length direction.

4. The reactor system according to claim 1, wherein for every pulse generator the electrodes attached to it are located in the reactor chamber in the central section such that they are, when measured in the length direction, at least a distance equalling 50% of the length of the central section apart.

5. The reactor system according to claim 1, having an entrance and an exit, whereby the central section lies between the opening and the exit such that a stream of a product can flow from the entrance to the exit.

6. The reactor system according to claim 1, whereby the electrodes are shaped and placed such that the electrical field in at least the central section is substantially homogeneous, whereby the field lines run in essentially the length direction.

7. The reactor system according to claim 1, whereby each pair of electrodes powers a separate segment along the length of the central section.

8. The reactor system according to claim 1, whereby at least one electrode is split into two or more split-electrodes.

9. The reactor system according to claim 1, whereby all pulse generators are bipolar pulse generators.

10. The reactor system according to claim 1, whereby all pulse generators are unipolar pulse generators.

11. The reactor system according to claim 9, whereby all pulse generators are Marx generators.

12. The reactor system according to claim 9, whereby all pulse generators include triggers for firing the pulse generators synchronously with a temporal uncertainty of not more than 30% of the pulse length.

13. The reactor system according to claim 1, whereby the pulse shape of each pair of electrodes is substantially equal.

14. A process for the electroporation of cells, comprising the steps of:

(1) providing a reactor system, comprising:
a reactor chamber having a length and a width, whereby the reactor chamber contains a central section along its length, wherein the length of the reactor chamber is at least 1.5 times the width of the reactor chamber;
a first pulse generator to which two electrodes (A1) and (A2) are connected, wherein the electrodes (A1) and (A2) are located in the reactor chamber in the central section at essentially opposite ends of the central section such that they are, when measured in the length direction, at least a distance equalling half the width of the reactor chamber apart; and
a second pulse generator to which two electrodes (B1) and (B2) are connected, wherein the electrodes (B1) and (B2) are located in the reactor chamber in the central section at essentially opposite ends of the central section such that they are, when measured in the length direction, at least a distance equalling half the width of the reactor chamber apart,
whereupon electrical field lines from said electrodes run essentially in the length direction of the reactor chamber whereby to produce a homogeneous electrical field the length of the reaction chamber, and
(2) sending a pulse to the electrodes to generate the homogeneous electric field;
(3) performing electroporation of the cells with the reactor system.

15. The process according to claim 14, wherein the cells comprise sugar beet cells.

16. The reactor system according to claim 10, whereby all pulse generators are Marx generators.

17. The reactor system according to claim 10, whereby all pulse generators include triggers for firing the pulse generators synchronously with a temporal uncertainty of not more than 30% of the pulse length.

18. The reactor system according to claim 11, whereby all pulse generators include triggers for firing the pulse generators synchronously with a temporal uncertainty of not more than 30% of the pulse length.

* * * * *